(12) United States Patent
Ishikawa et al.

(10) Patent No.: US 11,274,165 B2
(45) Date of Patent: Mar. 15, 2022

(54) PENTOSAN POLYSULFATE, PHARMACEUTICAL COMPOSITION, AND ANTICOAGULANT

(71) Applicant: OJI HOLDINGS CORPORATION, Tokyo (JP)

(72) Inventors: Kotaro Ishikawa, Tokyo (JP); Takuro Kashiwamura, Kanagawa (JP); Takuya Kato, Chiba (JP); Toru Koga, Saitama (JP); Suguru Ishikawa, Chiba (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 42 days.

(21) Appl. No.: 16/489,074

(22) PCT Filed: Feb. 27, 2018

(86) PCT No.: PCT/JP2018/007138
§ 371 (c)(1),
(2) Date: Aug. 27, 2019

(87) PCT Pub. No.: WO2018/159580
PCT Pub. Date: Sep. 7, 2018

(65) Prior Publication Data
US 2020/0062867 A1 Feb. 27, 2020

(30) Foreign Application Priority Data

Feb. 28, 2017 (JP) .............................. JP2017-035916
Aug. 31, 2017 (JP) .............................. JP2017-166559

(51) Int. Cl.
| | | |
|---|---|---|
| *C08B 37/02* | (2006.01) | |
| *A61K 31/737* | (2006.01) | |
| *A61P 7/02* | (2006.01) | |
| *C08B 37/00* | (2006.01) | |

(52) U.S. Cl.
CPC ........ *C08B 37/0057* (2013.01); *A61K 31/737* (2013.01); *A61P 7/02* (2018.01)

(58) Field of Classification Search
CPC ..... C08B 37/0057; C08B 37/14; C08B 37/00; A61K 31/7024; A61K 31/737; A61K 8/73; C08L 97/102; A61P 7/02; A61P 7/04
USPC ........................................................ 536/122
See application file for complete search history.

(56) References Cited

U.S. PATENT DOCUMENTS

| | | | |
|---|---|---|---|
| 4,168,742 | A | 9/1979 | Kluppel et al. |
| 4,699,900 | A | 10/1987 | Bayol et al. |
| 4,713,373 | A | 12/1987 | Bayol et al. |
| 4,727,063 | A | 2/1988 | Naggi et al. |
| 5,516,765 | A | 5/1996 | Andermann |
| 7,902,158 | B2 | 3/2011 | Kuszmann et al. |
| 8,987,216 | B2 | 3/2015 | Kuszmann et al. |
| 8,993,536 | B2 | 3/2015 | Kakehi et al. |
| 2001/0005720 | A1 | 6/2001 | Striker et al. |
| 2003/0109491 | A1 | 6/2003 | Ulmer et al. |
| 2006/0194759 | A1 | 8/2006 | Eidelson |
| 2007/0281893 | A1 | 12/2007 | Kuszmann et al. |
| 2008/0249298 | A1 | 10/2008 | Ulmer et al. |
| 2010/0055060 | A1 | 3/2010 | Yoshida et al. |
| 2010/0261807 | A1* | 10/2010 | Laine .................. C08L 5/14 523/122 |
| 2011/0118198 | A1 | 5/2011 | Kuszmann et al. |
| 2011/0251154 | A1* | 10/2011 | Stajic .................. A61P 19/02 514/54 |
| 2011/0281819 | A1 | 11/2011 | Kakehi et al. |
| 2011/0306567 | A1 | 12/2011 | Schofield et al. |

FOREIGN PATENT DOCUMENTS

| | | | | |
|---|---|---|---|---|
| CA | 2018133 | A1 | 12/1990 | |
| CN | 1051564 | A | 5/1991 | |
| CN | 1832966 | A | 9/2006 | |
| CN | 101014607 | A | 8/2007 | |
| CN | 102061323 | A | 5/2011 | |
| CN | 102300870 | A | 12/2011 | |
| CN | 102766225 | A * | 11/2012 | ............. C08B 37/14 |
| CN | 103320548 | A | 9/2013 | |
| CN | 105907896 | A | 8/2016 | |
| CN | 106832020 | A | 6/2017 | |
| EP | 0 116 801 | B1 | 4/1987 | |
| EP | 0889055 | A1 | 7/1999 | |
| JP | S48-043100 | B1 | 12/1973 | |
| JP | S60-063203 | A | 4/1985 | |
| JP | S61-130301 | A | 6/1986 | |
| JP | S61-130302 | A | 6/1986 | |
| JP | S61-197601 | A | 9/1986 | |
| JP | S62-004362 | B2 | 1/1987 | |
| JP | H03-20225 | A | 1/1991 | |
| JP | H09-509650 | A | 9/1997 | |
| JP | H10-195107 | A | 7/1998 | |
| JP | H11-049802 | A | 2/1999 | |
| JP | H11-180821 | A | 7/1999 | |

(Continued)

OTHER PUBLICATIONS

Office Action dated Nov. 16, 2020 in Australian Application No. 2018276567.
Office Action dated Apr. 27, 2021 in U.S. Appl. No. 16/646,243.
Stephan Daus et al., "Homogeneous Sulfation of Xylan from Different Sources", Macromolecular Materials and Engineering, 2011, vol. 296, pp. 551-561 (11 pages).
Elmiron®—100 mg (Pentosan Polysulfate Sodium)Capsules, 2002, [https://www.accessdata.fda.gov/drugsatfda_docs/label/2020/020193s014lbl.pdf] (14 pages).

(Continued)

*Primary Examiner* — Ganapathy Krishnan
(74) *Attorney, Agent, or Firm* — Sughrue Mion, PLLC

(57) ABSTRACT

The present invention provides pentosan polysulfate having a weight average molecular weight of 5000 or less and a content of acetyl groups of 0% to 2.0% by mass, or a pharmaceutically acceptable salt thereof, or a pharmaceutically acceptable solvate thereof. The pentosan polysulfate of the present invention, or a pharmaceutically acceptable salt thereof, or a pharmaceutically acceptable solvate thereof exhibits an anti-Xa activity and an anti-Xa/anti-IIa activity ratio, which are suitable for practical use, and is useful as a pharmaceutical composition such as an anticoagulant.

8 Claims, 1 Drawing Sheet

(56) References Cited

FOREIGN PATENT DOCUMENTS

| | | |
|---|---|---|
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 A2 | 11/2007 |
| WO | 2007/123800 A3 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | 2014/122251 A2 | 8/2014 |
| WO | 2014/122251 A3 | 8/2014 |
| WO | 2016/184887 A1 | 11/2016 |
| WO | 2016/191698 A1 | 12/2016 |
| WO | 2018/043667 A1 | 3/2018 |
| WO | 2018/043668 A1 | 3/2018 |

OTHER PUBLICATIONS

Office Action dated Mar. 25, 2021 issued by the Indian Patent Office in Indian Application No. 201947036653.

Extended European Search Report dated Feb. 3, 2021, from the European Patent Office in EP application No. 18809395.9, corresponding to U.S. Appl. No. 16/617,783.

"Technology of Wood Chemicals", CMC Publishing Co., Ltd., 2007, p. 108.

Koshijima, "Recent Problems of Hemicellulose Chemistry", Material, 1967, vol. 16, pp. 758-764.

International Preliminary Report on Patentability for PCT/JP2018/007138 dated Oct. 24, 2018 corresponding to the present application.

International Search Report for PCT/JP2018/007138 dated Mar. 27, 2018 corresponding to the present application.

Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).

Kabel et al., "Hydrothermally treated xylan rich by-products yield different classes of xylo-oligosaccharides" Carbohydrate Polymers, 2002, vol. 50, No. 1, pp. 47-56.

Kabel et al., "Complex xylo-oligosaccharides identified from hydrothermally treated Eucalyptus wood and brewery's spent grain", Carbohydrate Polymers, 2002, vol. 50, No. 2, pp. 191-200.

Koutaniemi et al., "Distinct roles of carbohydrate esterase family CE16 acetyl esterases and polymer-acting acetyl xylan esterases in xylan deacetylation" Journal of Biotechnology, 2013, vol. 168, No. 4, pp. 684-692.

Pawar et al., "Acetylation of woody lignocellulose: significance and regulation" Frontiers in Plant Science, 2013, vol. 4, No. 118, pp. 1-8.

International Search Report for PCT/JP2017/031434 dated Oct. 31, 2017 corresponding to U.S. Appl. No. 16/643,265.

Office Action issued by the Japanese Patent Office dated Apr. 18, 2017 in JP Application No. 2017-040067.

Office Action issued by the Japanese Patent Office dated Oct. 3, 2017 in JP Application No. 2017-166559.

Moure et al., "Advances in the manufacture, purification and applications of xylo-oligosaccharides as food additives and nutraceuticals", Process Biochemistry, 2006, vol. 41, Issue 9, pp. 1913-1923.

Gullón et al., "Structural features and properties of soluble products derived from Eucalyptus globulus hemicelluloses" Food Chemistry, 2011, vol. 127, No. 4, pp. 1798-1807.

Gullón et al., "Membrane processing of liquors from Eucalyptus globulus autohydrolysis" Journal of Food Engineering, 2008, vol. 87, No. 2, pp. 257-265.

Ishikawa et al., "Research and development of sulphated hemicellulose (PPS)", The 62nd Japan Technical Association of the Pulp and Paper Industry Annual Meeting, 2019, pp. 1-5.

Scully et al., "The antiheparin effect of a heparinoid, pentosane polysulphate" Biochem. J, 1984, vol. 218, pp. 657-665.

McCarty et al., "Sulfated glycosaminoglycans and glucosamine may synergize in promoting synovial hyaluronic acid synthesis" Medical Hypotheses, 2000, vol. 54, No. 5, pp. 798-802.

Ferrao et al., "The effect of heparin on cell proliferation and type-I collagen synthesis by adult human dermal fibroblasts" Biochimica et Biophysica Acta, 1993, vol. 1180, pp. 225-230.

International Search Report for PCT/JP2018/020644 dated Sep. 4, 2018, corresponding to U.S. Appl. No. 16/617,783.

International Search Report for PCT/JP2017/031433 dated Oct. 31, 2017 corresponding to U.S. Appl. No. 16/643,215.

Office Action issued by the Japanese Patent Office dated Jan. 8, 2019 in JP Application No. 2018-553269.

Office Action issued by the Japanese Patent Office dated Feb. 5, 2019 in JP Application No. 2018-229611.

Hirst et al., "Water-soluble Polysaccharides of Cladophora" Journal of the Chemical Society, 1965, pp. 2958-2967.

International Search Report for PCT/JP2018/033535 dated Nov. 27, 2018.

International Search Report for PCT/JP2018/046537 dated Mar. 5, 2019.

International Search Report for PCT/JP2017/031432 dated Oct. 31, 2017.

Office Action issued by the Japanese Patent Office dated Jul. 17, 2019 in JP Application No. 2018-516078.

Office Action issued by the Japanese Patent Office dated Jul. 17, 2019 in JP Application No. 2018-516079.

González et al., "Demonstration of Inhibitory Effect of Oral Shark Cartilage on Basic Fibroblast Growth Factor-Induced Angiogenesis in the Rabbit Cornea" Biol. Pharm. Bull, 2001, vol. 24, No. 2, pp. 151-154.

Swain et al., "Heparin-Binding Growth Factor Blockade with Pentosan Polysulfate" Annals of the New York Academy of Sciences, 1993, vol. 698, pp. 63-70.

Zugmaier et al., "Polysulfated Heparinoids Selectively Inactivate Heparin-Binding Angiogenesis Factors" Annals of the New York Academy of Sciences, 1999, vol. 886, pp. 243-248.

Zugmaier et al., "Inhibition by Pentosan Polysulfate (PPS) of Heparin-Binding Growth Factors Released From Tumor Cells and Blockage by PPS of Tumor Growth in Animals" Journal of the National Cancer Institute, 1992, vol. 84, No. 22, pp. 1716-1724.

Garrote et al., "Non-isothermal autohydroiysis of Eucalyptus wood", Wood Science and Technology, 2002, vol. 36, pp. 111-123.

Sivová et al., "Fagus sylvatica glucuronoxylan sulfate-chemical profile and pharmacological view" Starch, 2015, vol. 68, pp. 621-628.

Rhee et al., "Engineering the Xylan Utilization System in Bacillus subtilis for Production of Acidic Xylooligosaccharides" Applied and Environmental Microbiology, 2014, vol. 80, No. 3, pp. 917-927.

Maekawa et al., "Infrared Spectra of Wood Cellulose and Related Polysaccharide" Kyoto University, Research Institute Report, 1968, vol. 43, pp. 1-8.

(56) References Cited

OTHER PUBLICATIONS

Kabel et al., "In Vitro Fermentability of Differently Substituted Xylo-oligosaccharides" Journal of Agricultural and Food Chemistry, 2002, vol. 50, pp. 6205-6210.
Office Action issued by Japanese Patent Office dated Oct. 9, 2018 in JP Application No. 2018-516078 corresponding to the present application.
International Preliminary Report on Patentability dated Dec. 3, 2019 from the International Bureau in International Application No. PCT/JP2018/020644, corresponding to U.S. Appl. No. 16/617,783.
Takayuki Ohbuchi et al., "Structural Analysis of Neutral and Acidic Xylooligosaccharides from Hardwood Kraft Pulp, and Their Utilization by Intestinal Bacteria in Vitro", Bioscience, Biotechnology, and Biochemistry, vol. 73, No. 9, 2009, pp. 2070-2076 (8 pages total).
Office Action dated Jun. 2, 2021 from the United States Patent and Trademark Office in U.S. Appl. No. 16/643,215.
Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).
Extended European Search Report dated Feb. 26, 2021 from the European Patent Office in EP Application No. 17846672.8, corresponding to U.S. Appl. No. 16/643,265.
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371.2.
Mi et al., "Preparation of corn stover pentosan sulfate", Journal of Changchun University of Technology (Natural Science Edition), 2014, vol. 35, No. 6, pp. 716-719 (4 pages total).
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
Office Action dated Oct. 26, 2021 in U.S. Appl. No. 16/955,641.
Gura, "Cancer Models: Systems for Identifying New Drugs Are Often Faulty", Science, 1997, vol. 278, No. 5340, pp. 1041-1042 (6 pages total).
"The Merck Manual", Sixteenth Edition, 1992, pp. 339-342 and 1488-1490 (6 pages total).
Smith et al., "Cancer, inflammation and the AT1 and AT2 receptors", Journal of Inflammation, 2004, vol. 1, No. 3, pp. 1-12 (12 pages total).
Vergnolle et al., "Protease-activated receptors and inflammatory hyperalgesia", Mem Inst Oswaldo Cruz, Rio de Janeiro, 2005, vol. 100 (Suppl. I), pp. 173-176 (4 pages total).
Douglass et al., "1. Diagnosis, treatment and prevention of allergic disease: the basics", MJA Practice Essentials—Allergy, 2006, vol. 185, No. 4, pp. 228-233 (6 pages total).
Office Action dated Oct. 25, 2021 issued by China National Intellectual Property Administration in Chinese Patent Application No. 16646243.X, which corresponds to U.S. Appl. No. 16/646,243.
Office Action dated Jan. 4, 2022 from the Indian Patent Office in Indian Application No. 202047029636, corresponding to U.S. Appl. No. 16/955,641.

\* cited by examiner

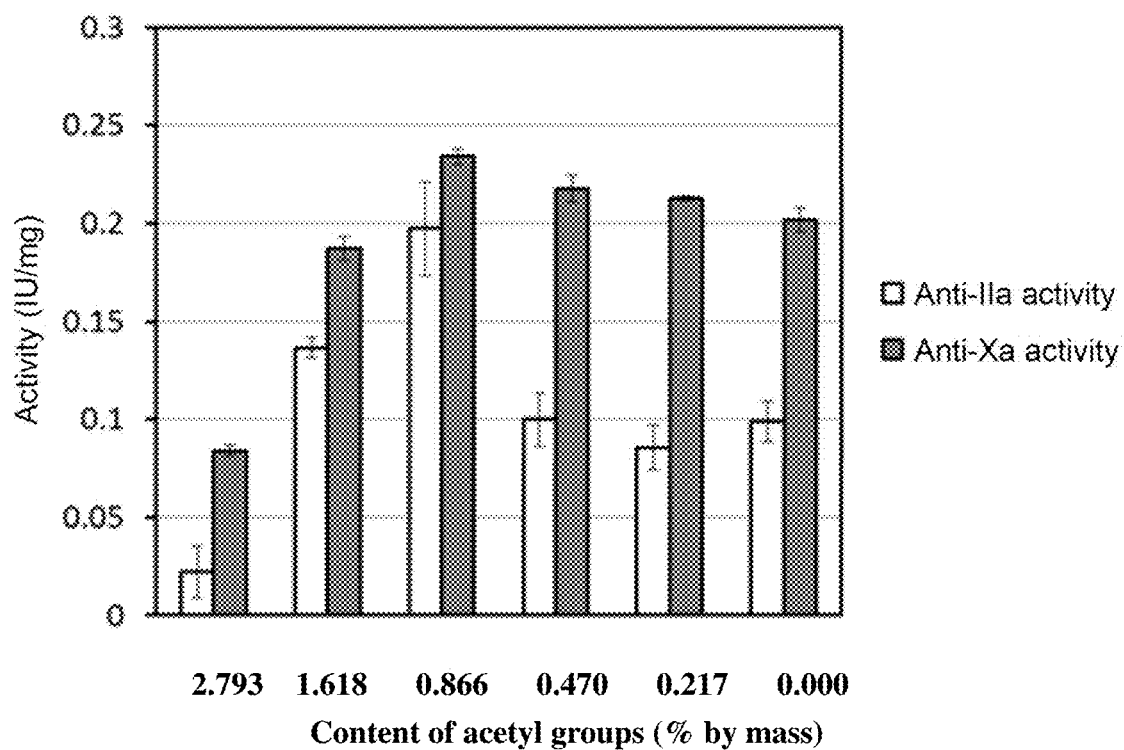

PENTOSAN POLYSULFATE, PHARMACEUTICAL COMPOSITION, AND ANTICOAGULANT

CROSS REFERENCE TO RELATED APPLICATIONS

This application is a National Stage of International Application No. PCT/JP2018/007138 filed on Feb. 27, 2018, which claims priority from Japanese Patent Application No. 2017-035916 filed on Feb. 28, 2017 and Japanese Patent Application No. 2017-166559 filed on Aug. 31, 2017.

TECHNICAL FIELD

The present invention relates to pentosan polysulfate, a pharmaceutical composition, and an anticoagulant.

BACKGROUND ART

Conventionally, heparin has been used as a therapeutic agent for thrombosis, osteoarthritis, and the like. However, since heparin is a substance separated from the organs of animals such as bovines or pigs, it is difficult to control the quality thereof. Moreover, from the viewpoint of religious ethics, etc., there may be a case where the use thereof is hesitated upon treatment. Thus, it has been desired to develop an alternative therapeutic agent that is free of animal-derived components and is used instead of heparin.

As such a substance used instead of heparin, for example, pentosan polysulfate has been known. Pentosan polysulfate is obtained by sulfurization of plant-derived xylooligosaccharide. Since such pentosan polysulfate is a substance free of animal-derived components, application of pentosan polysulfate as a therapeutic agent used instead of heparin has been expected (for example, Patent Document 1).

Xylan contained in hardwoods has been known to have an acetyl group at position 2 or position 3 at a ratio of 5 to 7 acetyl groups with respect to 10 xyloses in a natural condition (Non-Patent Document 1). In addition, Patent Document 2 discloses that pentosan polysulfate for medical use comprises a xylose unit, which binds to uronic acid at position 4 and is acetylated at position 3. From the content disclosed in Patent Document 3, it is considered that known activities of pentosan polysulfate are all activities of pentosan polysulfate that comprises a constant amount of acetyl groups. Accordingly, pentosan polysulfate having a low content of acetyl groups has not yet been provided, and the activity thereof has not yet been known, either.

PRIOR ART DOCUMENTS

Patent Documents

Patent Document 1: International Publication No. WO 2010/000013
Patent Document 2: International Publication No. WO 2014/114723

Non-Patent Documents

Non-Patent Document 1: CMC Publishing Co., Ltd., "*Wood Chemicals no Giyutsu* (Techniques of Wood Chemicals)," first edition issued in 2007, p. 108

SUMMARY OF INVENTION

Problem to be Solved by the Invention

It is a problem of the present invention to provide pentosan sulfate having an activity that is preferable for medical use.

Means for Solving the Problem

The present inventors have found that pentosan polysulfate having a low weight average molecular weight and a low content of acetyl groups has an Xa inhibitory activity and/or an anti-Xa/anti-IIa activity ratio that are higher than those of conventionally known pentosan polysulfate. The present inventors have completed the present invention based on these findings.

Specifically, the present invention has the following configuration.

[1] Pentosan polysulfate having a weight average molecular weight of 5000 or less and a content of acetyl groups of 0% to 2.0% by mass, or a pharmaceutically acceptable salt thereof, or a pharmaceutically acceptable solvate thereof.

[2] The pentosan polysulfate according to [1], which has a content of acetyl groups of 0% to 0.3% by mass, or a pharmaceutically acceptable salt thereof, or a pharmaceutically acceptable solvate thereof.

[3] The pentosan polysulfate according to [1] or [2], which has a weight average molecular weight of 4000 or less, or a pharmaceutically acceptable salt thereof, or a pharmaceutically acceptable solvate thereof.

[4] The pentosan polysulfate according to any one of [1] to [3], which has a structure represented by the following formula, a pharmaceutically acceptable salt thereof, or a pharmaceutically acceptable solvate thereof:

[Formula 1]

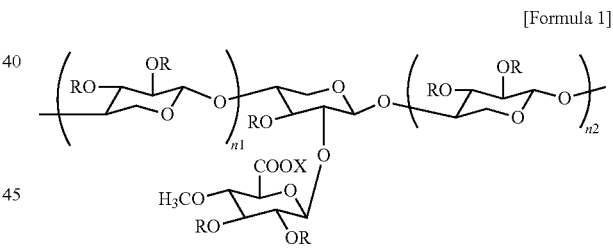

wherein R each independently represents a hydrogen atom or $-SO_3X^1$, and at least one R is $-SO_3X^1$, wherein $X^1$ represents a hydrogen atom or a monovalent or divalent metal; X represents a hydrogen atom or a monovalent or divalent metal; and n1 and n2 each independently represent an integer of 0 or more and 15 or less, and at least one of n1 and n2 is an integer of 1 or more.

[5] The pentosan polysulfate according to [4], wherein, in the above formula, X represents sodium, or a pharmaceutically acceptable salt thereof, or a pharmaceutically acceptable solvate thereof.

[6] The pentosan polysulfate according to any one of [1] to [5], which has a dispersion degree of 1.00 or more and 1.20 or less, or a pharmaceutically acceptable salt thereof, or a pharmaceutically acceptable solvate thereof.

[7] A pharmaceutical composition comprising, as an active ingredient, the pentosan polysulfate according to any one of [1] to [6], or a pharmaceutically acceptable salt thereof, or a pharmaceutically acceptable solvate thereof.

[8] An anticoagulant comprising, as an active ingredient, the pentosan polysulfate according to any one of [1] to [6], or a pharmaceutically acceptable salt thereof, or a pharmaceutically acceptable solvate thereof.

From other viewpoints, according to the present invention, the following is provided:

a method for inhibiting blood coagulation, comprising a step of applying an effective amount of the pentosan polysulfate according to any one of the above [1] to [6], or a pharmaceutically acceptable salt thereof, or a pharmaceutically acceptable solvate thereof;

use of the pentosan polysulfate according to any one of the above [1] to [6], or a pharmaceutically acceptable salt thereof, or a pharmaceutically acceptable solvate thereof, for production of an anticoagulant;

use of the pentosan polysulfate according to any one of the above [1] to [6], or a pharmaceutically acceptable salt thereof, or a pharmaceutically acceptable solvate thereof for inhibition of blood coagulation; and the pentosan polysulfate according to any one of the above [1] to [6], or a pharmaceutically acceptable salt thereof, or a pharmaceutically acceptable solvate thereof, which is used as an anticoagulant.

Effects of Invention

According to the present invention, pentosan polysulfate having an activity preferable for medical use is provided. Using the pentosan polysulfate of the present invention, a pharmaceutical composition and an anticoagulant can be provided.

BRIEF DESCRIPTION OF DRAWINGS

FIG. 1 is a graph showing the anti-IIa activity and anti-Xa activity of pentosan polysulfates having different contents of acetyl groups.

EMBODIMENTS OF CARRYING OUT THE INVENTION

Hereinafter, the present invention will be described in detail. The description for the components described below will be based on representative embodiments or specific examples; however, the present invention will not be limited to such embodiments.

(Pentosan Polysulfate)

Pentosan polysulfate is a compound obtained by sulfurization of at least one hydroxyl group of xylooligosaccharide. In the present description, pentosan polysulfate includes salts of pentosan polysulfate, solvates of pentosan polysulfate, and solvates of the salts of pentosan polysulfate. The salts of pentosan polysulfate are preferably pharmaceutically acceptable salts. Examples of such pharmaceutically acceptable salts may include pentosan polysulfate sodium, pentosan polysulfate potassium, and pentosan polysulfate calcium. The solvate is preferably a pharmaceutically acceptable solvate, and the solvent may be, for example, water.

Acidic xylooligosaccharide-derived pentosan polysulfate has a structure represented by the following formula. The pentosan polysulfate of the present invention may comprise one structure represented by the following formula, or may comprise two or more of the structures represented by the following formula. When the present pentosan polysulfate comprises two or more of the structures represented by the following formula, the following structure shows the repeating unit of pentosan polysulfate.

[Formula 2]

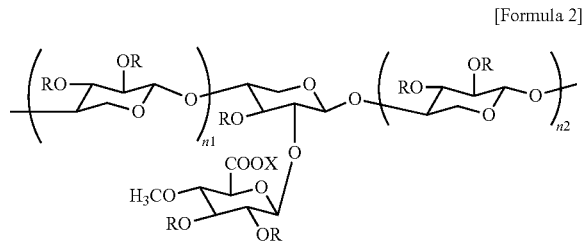

Herein, with regard to the pentosan polysulfate of the present invention represented by the above formula, R each independently represents a hydrogen atom, —COCH$_3$, or —SO$_3$X$^1$, and at least one R is —SO$_3$X$^1$. Herein, X$^1$ represents a hydrogen atom or a monovalent or divalent metal, preferably represents a hydrogen atom, sodium, potassium or calcium, more preferably represents sodium, potassium or calcium, and particularly preferably represents sodium. X represents a hydrogen atom or a monovalent or divalent metal, preferably represents sodium, potassium or calcium, and particularly preferably represents sodium. In addition, n1 and n2 each independently represent an integer of 0 or more and 15 or less, and at least one of n1 and n2 is an integer of 1 or more.

In the pentosan polysulfate of the present invention represented by the above formula, n1+n2 is preferably 1 to 15, more preferably 2 to 12, and further preferably 3 to 9.

In the above formula, X is preferably a monovalent or divalent metal, and is more preferably a pharmaceutically acceptable salt of pentosan polysulfate. For example, X is preferably sodium, potassium or calcium, and in this case, the salt of pentosan polysulfate includes pentosan polysulfate sodium, pentosan polysulfate potassium, and pentosan polysulfate calcium. Among others, the salt of pentosan polysulfate is particularly preferably pentosan polysulfate sodium.

The pentosan polysulfate of the present invention may comprise one structure represented by the above formula, or may comprise two or more of the structures represented by the above formula. When the present pentosan polysulfate comprises two or more of the structures represented by the above formula, the above structure shows the repeating unit of pentosan polysulfate.

In the pentosan polysulfate of the present invention, a portion that is the terminus of the structure represented by the above formula and does not bind to the structure represented by the above formula may be —OR. That is to say, —OR may bind to the left terminus (n1 side) of the above formula, whereas —R may bind to the right terminus (n2 side) of the above formula.

The pentosan polysulfate of the present invention is obtained by sulfurization of acidic xylooligosaccharide. Herein, the acidic xylooligosaccharide is formed by binding at least one uronic acid to at least any one xylose unit in a single molecule of xylooligosaccharide. That is, the acidic xylooligosaccharide has, as a side chain, at least one uronic acid residue in a single molecule of xylooligosaccharide. It is to be noted that the average number of uronic acid residues per molecule of acidic xylooligosaccharide is preferably 1 or more and 3 or less, and more preferably 1 or more and 2 or less. Herein, the number of uronic acid residues contained in a single molecule of acidic xylooligosaccharide can be measured by a carbazole-sulfuric acid method, or a colorimeteric method using sodium tetraborate.

Based on the aforementioned International Publication WO 2014/114723 and "*Wood Chemicals no Gijyutsu* (Techniques of Wood Chemicals)" (CMC Publishing Co., Ltd.), it is assumed that the known pentosan polysulfate would comprise a certain amount of xylose units, to which acetyl groups (—$COCH_3$) as well as uronic acid residue(s) bind. In the pentosan polysulfate of the present invention, the content of acetyl groups is reduced, and in particular, the content of acetyl groups binding to specific xylose units, as described above, is also reduced.

Specifically, the pentosan polysulfate of the present invention has a content of acetyl groups of 0% to 2.0% by mass. The content of acetyl groups in the pentosan polysulfate of the present invention is preferably 0% to 1.0% by mass, more preferably 0% to 0.4% by mass, further preferably 0% to 0.3% by mass, and particularly preferably, substantially 0% by mass. That is to say, the pentosan polysulfate of the present invention particularly preferably does not substantially comprise R that is —$COCH_3$ in the above formula.

As shown in Examples later, the content of acetyl groups in the pentosan polysulfate can be calculated from the integral ratio of peaks in $^1$H-NMR measurement. Specifically, first, the $^1$H-NMR measurement is carried out using a $^1$H-NMR measurement solution comprising a specific amount of pentosan polysulfate and a specific amount of internal standard substance. In the obtained spectrum, an integral ratio between the peak of a specific group of the internal standard substance and the peak of an acetyl group is obtained, and the molar amount of acetyl groups in the solution is then obtained. Thereafter, the molar amount of acetyl groups is multiplied by 43, and the obtained value is then divided by the average molecular weight obtained separately, so as to obtain % by mass.

The content of sulfur in the pentosan polysulfate of the present invention is preferably 10.0% by mass or more, more preferably 12.0% by mass or more, further preferably 15.5% by mass or more, and particularly preferably 16.5% by mass or more. On the other hand, the content of sulfur in the present pentosan polysulfate is preferably 20.0% by mass or less. Herein, the content of sulfur contained in the pentosan polysulfate is a value measured according to the oxygen flask combustion method described in the Japanese Pharmacopoeia.

The weight average molecular weight (Mw) of the pentosan polysulfate of the present invention is 5000 or less, and preferably 4000 or less. As shown in the after-mentioned Examples, the pentosan polysulfate of the present invention having a weight average molecular weight (Mw) of 5000 or less, and particularly, of 4000 or less, can obtain more preferred activity in medical use. The weight average molecular weight (Mw) of the pentosan polysulfate of the present invention may be, for example, 3900 or less, may also be 3800 or less, and may further be 3750 or less. In this case, the lower limit value of the weight average molecular weight (Mw) of the pentosan polysulfate is preferably 1000.

The number average molecular weight (Mn) of the pentosan polysulfate is preferably 5000 or less. It may be, for example, 4000 or less, may be 3900 or less, may also be 3800 or less, and may further be 3750 or less. In this case, the lower limit value of the number average molecular weight (Mn) of the pentosan polysulfate is preferably 300.

The weight average molecular weight (Mw) and the number average molecular weight (Mn) of the pentosan polysulfate of the present invention can be measured by GPC (gel permeation chromatography). As a GPC column, TSKgel G2000SWXL manufactured by Tosoh Corporation can be used. In addition, as conditions for GPC, the following conditions are adopted.

Eluent: 300 mM sodium chloride/50 mM sodium acetate buffer (pH 4.0)
Flow rate: 1 mL/min
Measurement temperature: 40° C.
Detector: differential refractive index detector
Analytical time: 15 minutes The dispersion degree of the pentosan polysulfate of the present invention is preferably 1.00 or more and 1.40 or less, and more preferably 1.00 or more and 1.35 or less. Also, the dispersion degree of the pentosan polysulfate is preferably 1.00 or more and 1.20 or less. Herein, the dispersion degree (D) of the pentosan polysulfate is calculated according to the following equation.

$$\text{Dispersion degree (D)} = \text{Weight average molecular weight (Mw)/Number average molecular weight (Mn)}$$

Pentosan polysulfate obtained by the after-mentioned production method has high purity, and its molecular weight distribution tends to be narrow. Moreover, the pentosan polysulfate obtained by the after-mentioned production method is excellent in terms of quality stability.

(Intended Use of Pentosan Polysulfate: Pharmaceutical Composition and Anticoagulant)

The pentosan polysulfate of the present invention can be used for intended uses such as pharmaceutical products, food products, and cosmetic products. For example, a pharmaceutical composition comprising, as an active ingredient, the pentosan polysulfate of the present invention (pentosan polysulfate, or a pharmaceutically acceptable salt thereof, or a solvate thereof) can be provided. In particular, since the present pentosan polysulfate has an anticoagulant activity, the above-described pharmaceutical composition can be used as an anticoagulant.

In general, anticoagulant activity is based on the activity of inhibiting blood coagulation factors. Specifically, when the anticoagulant activity is high, a blood coagulation reaction is inhibited. Blood coagulation factors mean the action system of a series of molecules in a living body for coagulating blood, when bleeding. A large number of blood coagulation factors are successively activated, so that fibrin is agglutinated and hemostasis is performed on the bleeding portion. Representative blood coagulation factors may include factor Xa and factor IIa, and blood coagulation can be inhibited by inhibiting these factors.

The factor Xa inhibitory activity (anti-Xa activity) of the pentosan polysulfate is preferably 0.10 IU/mg or more, and more preferably 0.12 IU/mg or more.

On the other hand, the factor IIa inhibitory activity (anti-IIa activity) of the pentosan polysulfate is preferably 0.50 IU/mg or less, more preferably 0.40 IU/mg or less, and further preferably 0.30 IU/mg or less.

Herein, the factor Xa inhibitory activity (anti-Xa activity) can be measured using Test Team (registered trademark) Heparin S (manufactured by Sekisui Medical Co., Ltd.).

Moreover, the factor IIa inhibitory activity (anti-IIa activity) can be measured using Biophen heparin anti-IIa (manufactured by Hyphen Biomed).

The activity ratio between the factor Xa inhibitory activity (anti-Xa activity) of the pentosan polysulfate and the factor IIa inhibitory activity (anti-IIa activity) thereof is preferably within a predetermined range. Specifically, the value of the anti-Xa activity/anti-IIa activity is preferably 0.50 or more, more preferably 1.00 or more, further preferably 1.10 or more, and still further preferably 1.20 or more.

In the pentosan polysulfate of the present invention, the values of the anti-Xa activity, the anti-IIa activity, and the anti-Xa activity/anti-IIa activity can be controlled within the above-described ranges. That is to say, in the pentosan polysulfate of the present invention, the anti-IIa activity can be suppressed to be lower than the anti-Xa activity. By controlling the value of anti-Xa activity/anti-IIa activity within the above-described range, the anticoagulant activity can be more effectively enhanced, and generation of side effects such as an increase in bleeding risk or a reduction in platelets can be suppressed.

A pharmaceutical composition comprising the pentosan polysulfate of the present invention can be used, for example, as a surface treatment agent for medical devices or medical materials. For example, the pharmaceutical composition comprising the pentosan polysulfate of the present invention can be used as a surface treatment agent for implantable artificial organs, artificial blood vessels, catheters, stents, blood bags, contact lenses, intraocular lenses, and surgical auxiliary instruments. As a method of immobilizing the pharmaceutical composition on the surface of a medical device or a medical material, for example, a method comprising allowing the pharmaceutical composition to come into contact with a medical device or a medical material, and then applying radioactive rays thereto, is applied.

Otherwise, the present pharmaceutical composition can also be used as an oral agent or an external preparation.

(Method for Producing Pentosan Polysulfate)

As an example, the pentosan polysulfate of the present invention can be obtained by a method for producing pentosan polysulfate, comprising a first step of obtaining acidic xylooligosaccharide from a plant-derived raw material, a second step of obtaining pentosan polysulfate from the acidic xylooligosaccharide, and also, a deacetylation step. Herein, the first step comprises a step of depolymerizing the plant-derived raw material. The step of depolymerizing the plant-derived raw material and a sulfurization step are carried out in this order, so that pentosan polysulfate can be efficiently produced. Further, by allowing the production method to comprise a deacetylation step, it becomes possible to reduce the costs of producing pentosan polysulfate with a low content of acetyl groups, and as a result, pentosan polysulfate can be provided at lower costs.

<Plant-Derived Raw Material>

In the present invention, the acidic xylooligosaccharide is obtained by depolymerization of a plant-derived raw material. Examples of the plant-derived raw material may include wood-derived raw materials, seed-derived raw materials, grain-derived raw materials, and fruit-derived raw materials. Moreover, examples of the plant-derived raw materials that can be used herein may also include cottons such as cotton linter or cotton lint, and herbaceous plants such as kenaf, hemp, ramie, or rice straw. As such a plant-derived raw material, the aforementioned raw materials derived from various products may be combined with one another and may be then used.

Among others, as a plant-derived raw material, a wood-derived raw material is preferably used. Examples of the wood-derived raw material may include wood raw materials such as softwoods or hardwoods. As a wood-derived raw material, at least one selected from softwoods and hardwoods are preferably used, and hardwoods are more preferably used. In addition, as such a wood-derived raw material, a mixture of softwoods and hardwoods may also be used. Moreover, as such a wood-derived raw material, a bark may also be used.

Examples of the hardwoods may include beech, *Eucalyptus globulus, Eucalyptus grandis, Eucalyptus eurograndis, Eucalyptus pellita, Eucalyptus braciana*, and *Acacia mearnsii*. Examples of the softwoods may include Japanese cedar, Japanese cypress, pine, hiba, and Japanese hemlock.

The specific gravity of the wood-derived raw material is preferably 450 kg/m$^3$ or more and 700 kg/m$^3$ or less, and more preferably 500 kg/m$^3$ or more and 650 kg/m$^3$ or less. By setting the specific gravity of the wood-derived raw material to be within the above-described range, the efficiency of producing acidic xylooligosaccharide can be further enhanced.

The wood-derived raw material is preferably wood chips obtained by crushing the aforementioned wood. By using wood chips as plant-derived raw materials, depolymerization of the plant-derived raw materials can be efficiently carried out, and the efficiency of producing acidic xylooligosaccharide can be enhanced.

<First Step>

[Depolymerization Step]

The step of depolymerizing a plant-derived raw material is a step of chemically and/or physically decomposing a plant-derived raw material to generate acidic xylooligosaccharide. Examples of the chemical and/or physical decomposition step may include a heat treatment step, an alkali treatment step, an acid treatment step, an enzyme treatment step, an ionic liquid treatment step, and a catalytic treatment step. Among these steps, the depolymerization step is preferably at least any one selected from a heat treatment step and an enzyme treatment step, and more preferably a heat treatment step. In addition, the heat treatment step may also be a heating and pressurizing step.

The depolymerization step is preferably carried out under non-alkaline conditions (which are, in the present description, pH 9 or less, preferably pH 8 or less, and more preferably pH 7 or less).

The heat treatment step is a step of heating a plant-derived raw material in the presence of a solution. In such a heat treatment step, since the plant-derived raw material is hydrolyzed, the heat treatment step may be referred to as a hydrolysis treatment step or a pre-hydrolysis treatment step. The solution used in the heat treatment step is preferably water, and the ratio (mass ratio) of the water to the plant-derived raw material is preferably 1:1 to 1:10. By setting the ratio of the water to the plant-derived raw material to be within the above-described range, the hydrolysis reaction can be efficiently carried out. The water used in the heat treatment step may be water, which is added separately from the plant-derived raw material, but a part of the water may be water originally contained in the plant-derived raw material.

In the heat treatment step, other drugs may also be added, as well as the plant-derived raw material and water. Examples of such other drugs may include alkali, acid, and a chelating agent. Moreover, drugs directly or indirectly assisting the depolymerization of polysaccharides, such as a scale inhibitor, a pitch control agent, and an ionic liquid, may also be added.

The heat treatment step is a step of heating a plant-derived raw material in the presence of water. The heating temperature (liquid temperature) applied in this step is preferably 30° C. or higher, more preferably 50° C. or higher, further preferably 75° C. or higher, still further preferably 90° C. or higher, particularly preferably 100° C. or higher, and most preferably 120° C. or higher. On the other hand, the heating temperature (liquid temperature) is preferably 300° C. or lower, more preferably 250° C. or lower, and further preferably 200° C. or lower.

The treatment time applied in the heat treatment step can be determined, as appropriate, depending on the treatment temperature. For example, the treatment time is preferably 5 minutes or more, more preferably 10 minutes or more, and further preferably 20 minutes or more. Besides, a P factor represented by the following expression is the product of the temperature and the time in the heating treatment. It is preferable to adjust the P factor within a preferred range.

$$P = \int_{t_0}^{t} \frac{k_{H1(T)}}{k_{100° \, C.}} \cdot dt = \int_{t_0}^{t} \mathrm{Exp} \cdot \left(40.48 - \frac{15106}{T}\right) \cdot dt \quad \text{[Expression 1]}$$

In the above expression, P indicates the P factor, T indicates the absolute temperature (° C.+273.5), t indicates the heat treatment time, and $K_{H1(T)}/K_{100° \, C.}$ indicates the relative rates of the hydrolysis of a glycoside bond.

In the heat treatment step, the P factor is set at preferably 200 or more, more preferably 250 or more, and further preferably 300 or more. On the other hand, the P factor is preferably 1000 or less. In the heat treatment step, the P factor is adjusted as appropriate, so that the average degree of polymerization of acidic xylooligosaccharide can be set to be within a desired range. By adjusting the average degree of polymerization of the acidic xylooligosaccharide, the weight average molecular weight is adjusted to 2000 or less, and preferably to 1600 or less, so that the molecular weight of the obtained pentosan polysulfate can be adjusted to 5000 or less, and preferably to 4000 or less.

In the heat treatment step, the pH value of a solution comprising a plant-derived raw material is preferably pH 9 or less, more preferably pH 8 or less, and further preferably pH 7 or less. That is, the heat treatment step is preferably carried out under non-alkaline conditions. It is to be noted that the above-described pH value indicates the pH of a solution before the heat treatment is performed.

In the heat treatment step, a raw material-derived acid may be dissociated, and acid hydrolysis may be at least partially carried out. Examples of the plant raw material-derived acid may include organic acids such as acetic acid and formic acid. In this case, the pH of the solution comprising a plant-derived raw material is further decreased after completion of the acid hydrolysis.

In the method for producing the pentosan polysulfate, the heat treatment is preferably established as a first step. By this step, the efficiency of producing acidic xylooligosaccharide can be enhanced, and further, the efficiency of producing the pentosan polysulfate can be enhanced. By establishing the heat treatment step as a first step, the number of steps necessary for obtaining acidic xylooligosaccharide can be significantly reduced, in comparison to the conventional method. Moreover, by establishing, as a first step, the heat treatment step performed under non-alkaline conditions, the acidic xylooligosaccharide is not replaced with hexenuronic acid, and thus, acidic xylooligosaccharide with suppressed coloration can be efficiently produced.

In the present invention, the depolymerization step is preferably a heat treatment step, but a step other than the heat treatment step can also be adopted as a depolymerization step. For example, when the depolymerization step is an enzyme treatment step, the depolymerization step comprises a step of mixing a plant-derived raw material with an enzyme. As such as enzyme, for example, hemicellulase or the like can be used. Specific examples of the enzyme that can be used herein may include: commercially available enzyme preparations such as Cellulosin HC100 (product name, manufactured by HBI Enzymes Inc.), Cellulosin TP25 (product name, manufactured by HBI Enzymes Inc.), Cellulosin HIC (product name, manufactured by HBI Enzymes Inc.), CALTAZYME (product name, manufactured by CLARIANT), ECOPULP (product name, manufactured by RHOM ENZYME), SUMIZYME (product name, manufactured by SHINNIHON CHEMICAL CO., LTD.), PULPZYME (manufactured by Novo Nordisk), and MULTIFECT 720 (Genencor); and xylanase produced by microorganisms belonging to genus Tricoderma, genus Termomyces, genus *Aureobasidium*, genus *Streptomyces*, genus *Aspergillus*, genus *Clostridium*, genus *Bacillus*, genus *Dermatoga*, genus *Thermoascus*, genus *Cardoceram*, genus *Thermomonospora*, etc.

In the enzyme treatment step, an enzyme is added into a solution prepared by mixing a plant-derived raw material with water. The temperature of the solution during the treatment is preferably 10° C. or higher and 90° C. or lower, and more preferably 30° C. or higher and 60° C. or lower. The temperature of the solution is preferably a temperature close to the optimal temperature of the used enzyme. Also, the pH of the solution is preferably adjusted to be within a range in which the activity of the enzyme is enhanced, and for example, the pH of the solution is preferably adjusted to pH 3 or more and pH 10 or less.

In addition, when the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. On the other hand, in the acid treatment step, hydrochloric acid, sulfuric acid, acetic acid, etc. is preferably added. Besides, in this case also, heating or pressurization may be carried out, as appropriate.

When the depolymerization step is at least any one selected from the enzyme treatment step, the alkali treatment step, and the acid treatment step, there may be a case where, after completion of the aforementioned step, a squeezing step, an extraction step, a heating step, a filtration step, a separation step, a purification step, a concentration step, a demineralization step, or the like are further established. Moreover, there may also be a case where, after completion of the aforementioned steps, a molecular weight reducing step is established. Besides, such other steps may include the steps described in JP 2003-183303 A, and these contents are incorporated into the present description.

[Filtration Step]

The first step may further comprise a filtration step after completion of the aforementioned depolymerization step. In the filtration step, the reaction product is separated into a solid content of the plant-derived raw material and a solution other than the solid content. Specifically, by establishing the filtration step after the depolymerization step, the reaction product is separated into a solid content used as a pulp raw material, and a filtrate. The solid content used as a pulp raw material is subjected to a digestion step or the like, which are performed as post-steps, so that it is converted to a cellulose raw material (dissolving pulp).

The recovered filtrate can be divided into a gas layer and a liquid layer. Since the gas layer contains large amounts of furfurals, these furfurals can be recovered and isolated. On the other hand, the liquid layer contains a large amount of hemicellulose comprising acidic xylooligosaccharide and neutral xylooligosaccharide. In the below-mentioned step, the acidic xylooligosaccharide contained in this liquid layer can be separated and purified.

[Separation/Purification Step]

The first step may further comprise a separation/purification step after completion of the aforementioned depolymerization step. When the first step comprises the aforementioned filtration step, the separation/purification step is preferably established after the filtration step.

In the first step, the separation/purification step may be established immediately after the depolymerization step. However, it is preferable that the filtration step be established after the depolymerization step, so as to establish a step of separating and purifying acidic xylooligosaccharide from the obtained filtrate. The filtration step may be established as a part of the separation/purification step, or may also be established as a first step that is independent from the separation/purification step. The separation/purification step is a step of separating and purifying acidic xylooligosaccharide. Since the filtrate obtained in the filtration step comprises neutral xylooligosaccharide or the like, as well as acidic xylooligosaccharide, the separation/purification step is also considered to be a step of removing such other saccharides, as necessary.

In the separation/purification step, it is preferable to adopt methods, such as, for example, ion exchange chromatography, affinity chromatography, gel filtration, an ion exchange treatment, an NF membrane treatment, a UF membrane treatment, an RO membrane treatment, and an activated carbon treatment. In the separation/purification step, it is also preferable to combine a plurality of the aforementioned methods with one another. Among others, by performing ion exchange chromatography in the separation/purification step, acidic xylooligosaccharide can be selectively separated and purified. In the ion exchange chromatography, by adsorbing acidic xylooligosaccharide, the acidic xylooligosaccharide can be mainly collected from the sugar liquid (filtrate). Specifically, the sugar liquid is first treated with a strong cation exchange resin, so that metal ions are removed from the sugar liquid. Subsequently, using a strong anion exchange resin, sulfate ions or the like are removed from the sugar liquid. Thereafter, the resulting sugar liquid is treated with a weak anion exchange resin, so that the acidic xylooligosaccharide is adsorbed on the resin. The acidic oligosaccharide adsorbed on the resin is eluted with low-concentration salts (NaCl, CaCl$_2$, KCl, MgCl$_2$, etc.), so that an acidic xylooligosaccharide solution containing small quantities of impurities can be obtained.

[Concentration Step]

The first step may further comprise a concentration step. It is preferable to establish such a concentration step, for example, after the filtration step and before the separation/purification step. By establishing such a concentration step, the separation/purification step can be more efficiently carried out, and the efficiency of producing the pentosan polysulfate can be enhanced.

Examples of the concentration step may include a membrane treatment step using an NF membrane, an ultrafiltration membrane, a reverse osmosis membrane, etc., and a concentration step or the like using evaporation or the like.

In the concentration step, the solution is concentrated, so that the content of the acidic xylooligosaccharide becomes preferably 10% or more and 80% or less, and more preferably 20% or more and 60% or less, with respect to the total mass of the concentrate.

[Dehydration Step]

The acidic xylooligosaccharide obtained in the first step may be in the form of an acidic xylooligosaccharide solution. However, by performing a dehydration step, the acidic xylooligosaccharide may also be obtained in the form of an acidic xylooligosaccharide concentrate or acidic xylooligosaccharide powders. In the case of producing acidic xylooligosaccharide powders, it is preferable to further establish a powderization step after completion of the separation/purification step. In the present invention, by establishing the dehydration step, sulfurization can be efficiently carried out in the after-mentioned sulfurization step.

In the powderization step, the acidic xylooligosaccharide solution obtained in the separation/purification step is treated, for example, using a spray dryer, a freeze-drying machine, a hot-air drying machine, or a water-soluble organic solvent, so that acidic xylooligosaccharide powders can be obtained.

<Second Step>

[Sulfurization Step]

In the second step, the acidic xylooligosaccharide obtained in the aforementioned steps is sulfurized. The acidic xylooligosaccharide obtained in the first step is sulfurized to obtain pentosan polysulfate.

The average degree of polymerization of the acidic xylooligosaccharide to be subjected to sulfurization is preferably adjusted, as appropriate, depending on the molecular weight of pentosan polysulfate obtained as a final product.

The average degree of polymerization of the acidic xylooligosaccharide can be calculated by dividing the total sugar amount of the acidic xylooligosaccharide by the amount of reducing sugar. Upon calculation of the total sugar amount, first, an acidic xylooligosaccharide solution is kept at 50° C., and is then centrifuged at 15000 rpm for 15 minutes. Thereafter, the total sugar amount of a supernatant is quantified by a phenol sulfuric acid method ("*Kangento no Teiryo-Ho* (Method of Quantifying Reducing Sugar)": Gakkai Shuppan Center). Herein, the used calibration curve is produced using D-xylose (Wako Pure Chemical Industries, Ltd.). Moreover, the amount of reducing sugar is quantified by a Somogyi-Nelson method ("*Kangento no Teiryo-Ho* (Method of Quantifying Reducing Sugar)"; Gakkai Shuppan Center). Also herein, the used calibration curve is produced using D-xylose (Wako Pure Chemical Industries, Ltd.).

In the sulfurization step, sulfuric acid or a sulfuric acid derivative is added to the acidic xylooligosaccharide solution to carry out sulfurization. Examples of the sulfuric acid derivative may include sulfur trioxide pyridine complex and chlorosulfonic acid. In this step, the concentration of the acidic xylooligosaccharide solution is preferably 0.1% by mass or more and 20% by mass or less, and it is preferable to add sulfuric acid to the acidic xylooligosaccharide solution having such a concentration to result in a concentration of 0.1% by mass or more and 50% by mass or less. After addition of sulfuric acid, the pH of the acidic xylooligosaccharide solution is preferably pH 1 or more and pH 9 or less.

[Post-Sulfurization Purification Step]

The second step may further comprise a post-sulfurization purification step after completion of the sulfurization. By establishing such a post-sulfurization purification step, pentosan polysulfate having high purity can be obtained.

In the post-sulfurization purification step, methods such as, for example, centrifugation, membrane filtration, dialysis, a water-soluble organic solvent treatment, and an activated carbon treatment are preferably adopted. Among these, the water-soluble organic solvent treatment and the activated carbon treatment are preferably used because sulfurized pentosan polysulfate can be selectively separated and purified according to these treatments.

[Powderization Step]

In the second step, the sulfurized pentosan polysulfate may be obtained in the form of a pentosan polysulfate solution. However, by subjecting the sulfurized pentosan polysulfate to a powderization step, it may be obtained in the form of pentosan polysulfate powders. In the case of producing pentosan polysulfate powders, it is preferable to further establish a powderization step after completion of the post-sulfurization purification step.

As a powderization step, the pentosan polysulfate solution obtained by the post-sulfurization purification step is treated, for example, using a spray dryer, a freeze-drying machine, a hot-air drying machine, or a water-soluble organic solvent, so that pentosan polysulfate powders can be obtained.

<Deacetylation Step>

A deacetylation step may be performed at any stage after completion of the depolymerization step. By such a deacetylation step, the content of acetyl groups in pentosan polysulfate can be reduced. Specifically, the deacetylation step is a step of adding bases to a solution comprising a substance obtained from a plant-derived raw material, such as acidic xylooligosaccharide (which is also referred to as a "solution comprising acidic xylooligosaccharide, etc." in the present description), so as to adjust the pH of the solution to pH 11 or more. In the deacetylation step, it may be adequate if the solution obtained after depolymerization, the filtrate obtained by the filtration step, the solution comprising acidic xylooligosaccharide after the separation/purification step and before the sulfurization step, a solution comprising acidic xylooligosaccharide (pentosan polysulfate) after the sulfurization step, etc. have pH 11 or more. Among these solutions, in a case where the solution comprising acidic xylooligosaccharide after the separation/purification step and before the sulfurization step is adjusted to have pH 11 or more, pentosan polysulfate with a reduced content of acetyl groups can be obtained with stable quality, and further, a site to which acetyl groups bind can also be sulfurized. Accordingly, the sulfurization efficiency, and further, the efficiency of producing the pentosan polysulfate can be improved. Moreover, when the solution comprising acidic xylooligosaccharide (pentosan polysulfate) obtained after the sulfurization step is adjusted to have pH 11 or more, the purification step can be efficiently promoted. The solution comprising acidic xylooligosaccharide, etc. is preferably an aqueous solution. In the present description, the solution comprising acidic xylooligosaccharide may also be referred to as an acidic xylooligosaccharide solution.

The pH value applied in the deacetylation step is preferably pH 11 to 14, and more preferably pH 12 to 13. The solution to be subjected to the deacetylation step is maintained preferably for 0.5 hours or more and at pH 11 or more, more preferably for 1.0 hour or more and at pH 11 or more, further preferably for 2.0 hours or more and at pH 11 or more, and particularly preferably for 3.0 hours or more and at pH 11 or more. In particular, when the pH value is less than 12, the solution is preferably maintained for 1.0 hour or more. Particularly preferred conditions may be conditions for maintaining the solution at pH 12 to 13 for 3 hours or more.

While the above-described solution is maintained in the above-described pH range, the solution is preferably stirred. The temperature applied while the solution is maintained in the above-described pH range is not particularly limited, but it is preferably room temperature.

In the deacetylation step, bases may be added to a solution to be subjected to the deacetylation step (a solution comprising acidic xylooligosaccharide, etc.). The added bases are not particularly limited, as long as the desired pH can be achieved. The added base is preferably sodium hydroxide.

The deacetylation step may comprise a pH adjustment step of adjusting the pH of a solution having pH 11 or more, which is obtained by maintaining the solution in the above-described pH range and then adding bases thereto, to a pH value of less than 11. In the pH adjustment step, the pH value of the solution may be adjusted to, for example, pH 9 or less, pH 8 or less, pH 7 or less, pH 6 or less, pH 5 or less, pH 4 or less, or the like. The adjustment may be carried out by addition of an acid. An example of the acid used is hydrochloric acid.

The deacetylation step preferably comprises a demineralization step after completion of the above-described pH adjustment step. Demineralization can be carried out, for example, using a dialysis membrane or an NF membrane.

The deacetylation step may further comprise a step of powdering the obtained product for the subsequent treatment.

<Other Steps>

[Molecular Weight Adjustment Step]

A molecular weight adjustment step may be established between the aforementioned first step and second step. The molecular weight adjustment step may be carried out either before or after the deacetylation step. In the molecular weight adjustment step, the molecular weight of the acidic xylooligosaccharide obtained in the first step is adjusted. For example, in the molecular weight adjustment step, the molecular weight of the acidic xylooligosaccharide is reduced, so that the weight average molecular weight thereof is set to be preferably 2000 or less, and more preferably to 1600 or less.

In the molecular weight adjustment step, for example, an acid treatment, an alkali treatment, an enzyme treatment, an NF membrane treatment, a UF membrane treatment, an RO membrane treatment, a gel filtration treatment, an activated carbon treatment, an ion exchange treatment, an electrodialysis treatment, or the like is carried out, so that pentosan polysulfate having a desired weight average molecular weight can be obtained. Moreover, in the molecular weight adjustment step, a method of performing a membrane treatment to selectively recover pentosan polysulfate having a desired weight average molecular weight may also be adopted.

[Post-Molecular Weight Adjustment Separation/Purification Step]

The method for producing the pentosan polysulfate may further comprise a post-molecular weight adjustment separation/purification step, after completion of the molecular weight adjustment step. Examples of the post-molecular weight adjustment separation/purification step may include gel filtration, an ion exchange treatment, an NF membrane treatment, a UF membrane treatment, an RO membrane treatment, an electrodialysis treatment, an activated carbon treatment, a water-soluble organic solvent treatment, and a chromatographic treatment. By establishing such a post-molecular weight adjustment separation/purification step, the acidic xylooligosaccharide having a desired molecular weight obtained in the molecular weight adjustment step can be selectively recovered, and thus, pentosan polysulfate having narrow molecular weight distribution can be efficiently obtained.

EXAMPLES

Hereinafter, the features of the present invention will be described more specifically with reference to the following Production Examples. The materials, used amounts, proportions, treatment content, treatment procedures, or the like shown in the following Production Examples can be appropriately changed to the extent that such changes do not depart from the spirit of the present invention. Therefore, the scope of the present invention should not be construed as being limited by the following specific examples.

Examples 1 to 5: Influence of Content of Acetyl Groups

<Production of Acidic Xylooligosaccharide>

40 Parts by mass of water was added to 10 parts by mass of wood chips (hardwoods), and the resulting wood chips were then heat-treated at 160° C. for 3 hours. Thereafter, using Screw Press (manufactured by Shinryo Corporation; 250×1000 SPH-EN), solid-liquid separation was carried out, and the filtrate was then recovered. The filtrate was filtrated through a bag filter with a micron rate of 1 μm (manufactured by ISP Filters), and 5 parts by mass of activated carbon (manufactured by Mikura Kasei Kabushiki Kaisha; PM-SX) was added to the obtained filtrate, followed by treating at 50° C. for 2 hours. Thereafter, the reaction mixture including the activated carbon was further filtrated through a ceramic filter with a micron rate of 0.2 μm (manufactured by Nihon Pall Co., Ltd.) to recover a clear filtrate. The clear filtrate was 20 times concentrated using a reverse osmosis membrane (manufactured by NITTO DENKO CORPORATION; NTR-7450) to obtain a concentrated sugar liquid. The concentrated sugar liquid was passed through a 4-bed 4-tower type ion exchange resin consisting of a strong cationic resin (manufactured by Mitsubishi Chemical Corporation: PK-218), a weak anionic resin (manufactured by Mitsubishi Chemical Corporation; WA30), a strong cationic resin (manufactured by Mitsubishi Chemical Corporation; PK-218), and a weak anionic resin (manufactured by Mitsubishi Chemical Corporation; WA30) at SV 1.5. Acidic xylooligosaccharide was adsorbed on the weak anionic resins of the second and fourth towers, and thereafter, a 50 mM sodium chloride aqueous solution was passed through the second and fourth towers at SV 1.5, thereby recovering an acidic xylooligosaccharide solution having an average degree of polymerization of less than 8. To the obtained acidic xylooligosaccharide solution, sodium hydroxide was added to achieve the pH shown in the table, and the mixed solution was then stirred for the period of time shown in the table to carry out deacetylation. To the obtained solution, hydrochloric acid was added to achieve the pH value that was less than 5, and demineralization was then carried out using a dialysis membrane (manufactured by SPECTRUM; Spectra/Pore). The obtained acidic xylooligosaccharide solution was powdered using a freeze-drying machine (manufactured by EYELA).

<Production of Pentosan Polysulfate Sodium>

To a 100-mL separable flask, 10 mL of N,N-dimethylformamide, 2.4 g of a sulfur trioxide pyridine complex, and 0.3 g of the acidic xylooligosaccharide powders produced by the aforementioned method were added, and the obtained mixture was then reacted at 40° C. for 3 hours. After cooling, the obtained reaction mixture was added dropwise into 500 mL of ethanol, the generated precipitate was then collected by filtration, and 30 mL of water was then added to the precipitate to dissolve it therein. A sodium hydroxide solution was added to the obtained solution to adjust the pH value to pH 10. The resulting solution was added dropwise into 500 mL of ethanol, and the obtained precipitate was then collected by filtration. Thereafter, 50 mL of water was added thereto to dissolve the precipitate therein, and activated carbon was then added to the solution, followed by stirring and filtration. Thereafter, the filtrate was concentrated using an evaporator, and was then powdered using a freeze-drying machine (manufactured by EYELA).

<Content of Acetyl Groups>

35 mg of Sodium 3-(trimethylsilyl)propionate-2,2,3,3-d4 (ISOTEC) was dissolved in heavy water (KANTO KAGAKU), and using a 25 mL measuring flask, the solution was diluted to prepare an internal standard solution. The pentosan polysulfate sodium in each of Examples and Comparative Examples was weighed (30 mg), and it was then dissolved in 1 mL of the internal standard solution, so as to prepare a solution for use in NMR. The obtained solution was transferred into an NMR sample tube (KANTO KAGAKU), and the $^1$H-NMR measurement was then carried out using FT-NMR (JNM-LA400; JEOL Ltd.). Based on the integral ratio between the trimethylsilyl group peak of the internal standard substance and the acetyl group peak of the pentosan polysulfate sodium, the content of acetyl groups was calculated.

<Weight Average Molecular Weight>

The weight average molecular weight (Mw) of pentosan polysulfate shown in Table 1 was measured by GPC (gel permeation chromatography). As a GPC column, YMC-Pack Diol-300 and YMC-Pack Diol-60 (manufactured by YMC) were connected with each other and were used. The measurement was carried out under the following conditions.

Eluent: 25 mM potassium dihydrogen phosphate/25 mM dipotassium hydrogen phosphate/50 mM potassium chloride Flow rate: 0.7 mL/min Measurement temperature: 40° C.

Detector: differential refractive index detector

Analytical time: 40 minutes

<Content of Sulfur>

According to the oxygen flask combustion method described in the Japanese Pharmacopoeia, the content of sulfur in pentosan polysulfate sodium was measured.

<Measurement of Anti-Xa Activity>

Using Test Team (registered trademark) Heparin S (manufactured by Sekisui Medical Co., Ltd.), the anti-Xa activity of pentosan polysulfate sodium was measured.

<Measurement of Anti-IIa Activity>

Using Biophen heparin anti-IIa (manufactured by Hyphen Biomed), the anti-IIa activity of pentosan polysulfate sodium was measured.

TABLE 1

|  | Comp. Ex. 1 | Ex. 1 | Ex. 2 | Ex. 3 | Ex. 4 | Ex. 5 |
| --- | --- | --- | --- | --- | --- | --- |
| Deacetylation conditions | Not treated | pH 11, 1 hr | pH 11, 2 hr | pH 12, 0.5 hr | pH 12, 1 hr | pH 13, 3 hr |
| Weight average molecular weight | 2211 | 2356 | 2325 | 2178 | 2129 | 2155 |

TABLE 1-continued

|  | Comp. Ex. 1 | Ex. 1 | Ex. 2 | Ex. 3 | Ex. 4 | Ex. 5 |
|---|---|---|---|---|---|---|
| Content of acetyl groups (% by mass) | 2.793 | 1.618 | 0.866 | 0.470 | 0.217 | 0.000 |
| Content of sulfur (% by mass) | 16.27 | 14.33 | 15.12 | 15.09 | 15.34 | 15.28 |
| Anti-IIa activity (IU/mg) | 0.0221 | 0.1405 | 0.1845 | 0.0676 | 0.0934 | 0.0976 |
| Anti-Xa activity (IU/mg) | 0.0840 | 0.2047 | 0.2588 | 0.2439 | 0.2419 | 0.2297 |
| Anti-Xa/anti-IIa activity ratio | 3.801 | 1.457 | 1.403 | 3.607 | 2.591 | 2.352 |

The anti-IIa activity and anti-Xa activity shown in Table 1 are also shown in a graph (FIG. 1).

As is found from the results shown in Table 1 and FIG. 1, the pentosan polysulfate sodium of the Examples having a low content of acetyl groups exhibited a favorable anti-Xa/anti-IIa activity ratio, and the anti-Xa activity thereof was higher than that of the pentosan polysulfate sodium of the Comparative Examples, which was not subjected to a deacetylation treatment.

When pentosan polysulfate sodium powders were obtained from the acidic xylooligosaccharide powders under the conditions of Comparative Example 1 and Example 5, the yields were as shown in Table 2.

TABLE 2

| Comp. Ex. 1 | Ex. 5 |
|---|---|
| Approx. 18.1% (Yield: 0.1391 g, added amount: 0.3072 g) | Approx. 40.9% (Yield: 0.3181 g, added amount: 0.3108 g) |

Examples 6 to 8: Influence of Molecular Weight

Example 6

<Production of Acidic Xylooligosaccharide>

40 Parts by mass of water was added to 10 parts by mass of wood chips (hardwoods), and the resulting wood chips were then heat-treated at 160° C. for 3 hours. Thereafter, using Screw Press (manufactured by Shinryo Corporation: 250×1000 SPH-EN), solid-liquid separation was carried out, and the filtrate was then recovered. The filtrate was filtrated through a bag filter with a micron rate of 1 μm (manufactured by ISP Filters), and 5 parts by mass of activated carbon (manufactured by Mikura Kasei Kabushiki Kaisha; PM-SX) was added to the obtained filtrate, followed by treating at 50° C. for 2 hours. Thereafter, the reaction mixture including the activated carbon was further filtrated through a ceramic filter with a micron rate of 0.2 μm (manufactured by Nihon Pall Co., Ltd.) to recover a clear filtrate. The clear filtrate was 20 times concentrated using a reverse osmosis membrane (manufactured by NITTO DENKO CORPORATION; NTR-7450) to obtain a concentrated sugar liquid. The concentrated sugar liquid was passed through a 4-bed 4-tower type ion exchange resin consisting of a strong cationic resin (manufactured by Mitsubishi Chemical Corporation; PK-218), a weak anionic resin (manufactured by Mitsubishi Chemical Corporation; WA30), a strong cationic resin (manufactured by Mitsubishi Chemical Corporation; PK-218), and a weak anionic resin (manufactured by Mitsubishi Chemical Corporation; WA30) at SV 1.5. Acidic xylooligosaccharide was adsorbed on the weak anionic resins of the second and fourth towers, and thereafter, a 50 mM sodium chloride aqueous solution was passed through the second and fourth towers at SV 1.5, thereby recovering an acidic xylooligosaccharide solution. To the obtained acidic xylooligosaccharide solution, sodium hydroxide was added to achieve pH 13, and the mixed solution was then stirred for 3 hours to carry out deacetylation. To the obtained solution, hydrochloric acid was added to achieve the pH value that was less than 5, and demineralization was then carried out using a dialysis membrane (manufactured by SPECTRUM; Spectra/Pore). The obtained acidic xylooligosaccharide solution was powdered using a freeze-drying machine (manufactured by EYELA).

<Production of Pentosan Polysulfate Sodium>

To a 100-mL separable flask, 25 mL of N,N-dimethylformamide, 10 g of a sulfur trioxide pyridine complex, and 2 g of the acidic xylooligosaccharide powders produced by the aforementioned method were added, and the obtained mixture was then reacted at 40° C. for 3 hours. After cooling, the obtained reaction mixture was added dropwise into 200 mL of ethanol, the generated precipitate was then collected by filtration, and 10 mL of water was then added to the precipitate to dissolve it therein. A sodium hydroxide solution was added to the obtained solution to adjust the pH value to pH 10. The resulting solution was added dropwise into 200 mL of ethanol, and the obtained precipitate was then collected by filtration. Thereafter, 10 mL of water was added to the precipitate to dissolve it therein, and activated carbon was then added to the solution, followed by stirring and filtration. The operation to add the obtained filtrate added dropwise into 200 mL of ethanol and then to collect the precipitate by filtration was repeated three times to carry out purification. Thus, the pentosan polysulfate sodium of Example 6 was obtained.

Example 7

Pentosan polysulfate sodium was obtained in the same manner as that of Example 6, with the exception that, in the above section <Production of acidic xylooligosaccharide>, 40 parts by mass of water was added to 10 parts by mass of wood chips (hardwoods) and the resulting wood chips were then heat-treated at 160° C. for 2 hours.

Example 8

Pentosan polysulfate sodium was obtained in the same manner as that of Example 6, with the exception that, in the above section <Production of acidic xylooligosaccharide>, 40 parts by mass of water was added to 10 parts by mass of wood chips (hardwoods) and the resulting wood chips were then heat-treated at 150° C. for 2 hours.

Comparative Example 2

(Beech-derived) pentosan polysulfate sodium that was a commercially available product was used as pentosan polysulfate sodium.

Comparative Example 3

50 Parts by weight of 3 N sodium hydroxide was added to 10 parts by mass of wood chips (broad leaf tree), and the resulting wood chips were then heat-treated at 155° C. for 2 hours. After cooling, using Screw Press (manufactured by Shinryo Corporation; 250×1000 SPH-EN), solid-liquid separation was carried out. The obtained solid residue was washed with ion exchange water three times. 100 Parts by mass of 1 N sodium hydroxide was added to 10 parts by weight of the obtained solid residue, followed by performing a heat treatment at 70° C. for 3 hours. Thereafter, using Screw Press (manufactured by Shinryo Corporation; 250× 1000 SPH-EN), solid-liquid separation was carried out, and the filtrate was then recovered. 1 N hydrochloric acid was added to this filtrate to neutralize it, and the obtained precipitate was then collected by filtration. The obtained precipitate was fully washed with ion exchange water, and was then dried under reduced pressure. Other than those as described above, pentosan polysulfate sodium was obtained in the same manner as that of Example 6.

Comparative Example 4

A commercially available product, Cartrophen Vet (registered trademark) (manufactured by DS Pharma Animal Health), was subjected to demineralization using a dialysis membrane (manufactured by SPECTRUM; Spectra/Pore), and was then powdered using a freeze-drying machine (manufactured by EYELA) to obtain pentosan polysulfate sodium.

(Analysis and Evaluation)

The weight average molecular weight (Mw) of the pentosan polysulfate sodium obtained in each of Examples 6 to 8 and Comparative Examples 2 to 4 was measured by GPC (gel permeation chromatography). As a GPC column, TSKgel G2000SWXL manufactured by Tosoh Corporation was used, and the measurement was carried out under the following conditions.

Eluent: 300 mM sodium chloride/50 mM sodium acetate buffer (pH 4.0)
Flow rate: 1 mL/min
Measurement temperature: 40° C.
Detector: differential refractive index detector
Analytical time: 15 minutes The content of acetyl groups, the content of sulfur, the anti-Xa activity, and the anti-IIa activity were measured in the same manners as those of Examples 1 to 5.

TABLE 3

|  | Ex. 6 | Ex. 7 | Ex. 8 | Comp. Ex. 2 | Comp. Ex. 3 | Comp. Ex. 4 |
| --- | --- | --- | --- | --- | --- | --- |
| Weight average molecular weight (Mw) | 3705 | 3553 | 4364 | 7344 | 25487 | 7279 |
| Content of acetyl groups (% by mass) | 0.000 | 0.000 | 0.000 | 0.000 | 0.000 | 0.307 |
| Dispersion degree | 1.16 | 1.18 | 1.19 | 1.43 | 1.31 | 1.46 |
| Content of sulfur (% by mass) | 18.8 | 16.7 | 16.3 | 15.3 | 15.3 | 15.4 |
| Anti-Xa activity (IU/mg) | 0.67 | 0.15 | 0.22 | 1.69 | 16.61 | 0.73 |
| Anti-IIa activity (IU/mg) | 0.15 | 0.12 | 0.43 | 15.52 | 62.12 | 6.80 |
| Anti-Xa/anti-IIa activity ratio | 4.29 | 1.25 | 0.51 | 0.11 | 0.15 | 0.11 |

As shown in Table 3, in the pentosan polysulfate sodium of all of the Examples and Comparative Examples, the content of acetyl groups was low, the anti-Xa activity was sufficiently high. In addition, the pentosan polysulfate sodium of Examples 6 to 8 having a weight average molecular weight of 5000 or less, exhibited a high anti-Xa/anti-IIa activity ratio.

The invention claimed is:

1. A pentosan polysulfate having a weight average molecular weight of 5000 or less and a content of acetyl groups of 0% to 0.3% by mass, or a pharmaceutically acceptable salt thereof, or a pharmaceutically acceptable solvate thereof.

2. The pentosan polysulfate according to claim 1, which has a content of acetyl groups of 0% by mass, or a pharmaceutically acceptable salt thereof, or a pharmaceutically acceptable solvate thereof.

3. The pentosan polysulfate according to claim 1, which has a weight average molecular weight of 4000 or less, or a pharmaceutically acceptable salt thereof, or a pharmaceutically acceptable solvate thereof.

4. The pentosan polysulfate according to claim 1, which has a structure represented by the following formula, a pharmaceutically acceptable salt thereof, or a pharmaceutically acceptable solvate thereof:

[Formula 1]

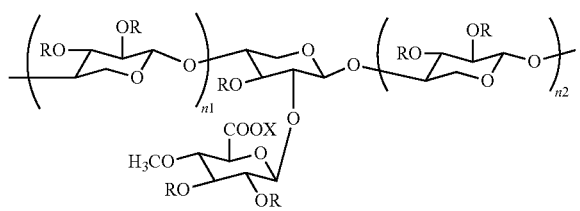

wherein R each independently represents a hydrogen atom or —SO$_3$X$^1$, and at least one R is —SO$_3$X$^1$, wherein X$^1$ represents a hydrogen atom or a monovalent or divalent metal; X represents a hydrogen atom or a monovalent or divalent metal; and n1 and n2 each independently represent an integer of 0 or more and 15 or less, and at least one of n1 and n2 is an integer of 1 or more.

5. The pentosan polysulfate according to claim 4, wherein, in Formula 1, X represents sodium, or a pharmaceutically acceptable salt thereof, or a pharmaceutically acceptable solvate thereof.

6. The pentosan polysulfate according to claim 1, which has a dispersion degree of 1.00 or more and 1.20 or less, or a pharmaceutically acceptable salt thereof, or a pharmaceutically acceptable solvate thereof.

7. A pharmaceutical composition comprising, as an active ingredient, the pentosan polysulfate according to claim 1, or a pharmaceutically acceptable salt thereof, or a pharmaceutically acceptable solvate thereof.

8. A method for inhibiting blood coagulation, comprising: administrating to a subject in need thereof an effective amount of the pentosan polysulfate according to claim 1, or a pharmaceutically acceptable salt thereof, or a pharmaceutically acceptable solvate thereof.

* * * * *